(12) United States Patent
Lee et al.

(10) Patent No.: US 11,986,545 B2
(45) Date of Patent: May 21, 2024

(54) FUSION PROTEIN COMPRISING GROWTH DIFFERENTIATION FACTOR 11 AND EPIDERMAL GROWTH FACTOR WITH ENHANCED ANTI-OXIDATION ACTIVITY AND ENHANCED SKIN CELL PROLIFERATION EFFECT AND COSMETIC COMPOSITION FOR ANTI-WRINKLE COMPRISING THE SAME AS EFFECTIVE COMPONENT

(71) Applicants: NEXGEN BIOTECHNOLOGIES, INC., Seoul (KR); Sun Kyo Lee, Gyeonggi-do (KR)

(72) Inventors: Sun Kyo Lee, Gyeonggi-do (KR); Seong Ran Lee, Gyeonggi-do (KR); Han Bong Ryu, Seoul (KR); Tae Hyun Kim, Gyeonggi-do (KR)

(73) Assignees: NEXGEN BIOTECHNOLOGIES, INC., Seoul (KR); Sun Kyo Lee, Gyeonggi-Do (KR)

( * ) Notice: Subject to any disclaimer, the term of this patent is extended or adjusted under 35 U.S.C. 154(b) by 783 days.

(21) Appl. No.: 17/599,061

(22) PCT Filed: Jun. 1, 2017

(86) PCT No.: PCT/KR2017/005751
§ 371 (c)(1),
(2) Date: Sep. 28, 2021

(87) PCT Pub. No.: WO2018/216842
PCT Pub. Date: Nov. 29, 2018

(65) Prior Publication Data
US 2022/0160609 A1 May 26, 2022

(30) Foreign Application Priority Data

May 26, 2017 (KR) ........................ 10-2017-0065257

(51) Int. Cl.
| | | |
|---|---|---|
| A61K 38/00 | (2006.01) | |
| A61K 8/64 | (2006.01) | |
| A61Q 19/08 | (2006.01) | |
| C07K 14/485 | (2006.01) | |
| C12N 15/70 | (2006.01) | |

(52) U.S. Cl.
CPC ................ A61K 8/64 (2013.01); A61Q 19/08 (2013.01); C07K 14/485 (2013.01); C12N 15/70 (2013.01); C07K 2319/00 (2013.01); C12N 2800/22 (2013.01)

(58) Field of Classification Search
CPC .... A61K 8/64; A61K 2800/522; A61Q 19/08; C07K 14/475; C07K 14/485; C07K 2319/00; C12N 15/70; C12N 2800/22
See application file for complete search history.

(56) References Cited

FOREIGN PATENT DOCUMENTS

| | | |
|---|---|---|
| JP | 2006-083178 A | 3/2006 |
| KR | 10-2013-0138563 A | 12/2013 |
| KR | 10-1609041 B1 | 4/2016 |
| KR | 10-01652956 B1 | 8/2016 |
| KR | 10-1678392 B1 | 11/2016 |
| WO | WO 2013/184939 A2 | 12/2013 |
| WO | WO 2014/062424 A1 | 4/2014 |

OTHER PUBLICATIONS

International Search Report for PCT/KR2017/005751 dated Feb. 19, 2018.
Hanahan, D., "Studies on Transformation of *Escherichia coli* with Plasmids", J. Mol. Biol. vol. 166, 557-580, 1983.

*Primary Examiner* — Aradhana Sasan
*Assistant Examiner* — Mercy H Sabila
(74) *Attorney, Agent, or Firm* — The PL Law Group, PLLC

(57) ABSTRACT

A fusion protein according to an embodiment of the present disclosure includes a growth differentiation factor 11 and an epidermal growth factor with an enhanced anti-oxidation activity and an enhanced skin cell proliferation effect, A cosmetic composition according to an embodiment of the present disclosure includes the fusion protein as an effective component. The cosmetic composition can be advantageously used in future as a material of a functional cosmetic product.

19 Claims, 3 Drawing Sheets
Specification includes a Sequence Listing.

Diagram showing expression of fusion protein comprising GDF11 and EGF

SEQUENCE LISTING

```
<160> NUMBER OF SEQ ID NOS: 8

<210> SEQ ID NO 1
<211> LENGTH: 486
<212> TYPE: DNA
<213> ORGANISM: Artificial Sequence
<220> FEATURE:
<223> OTHER INFORMATION: GDF11-EGF fusion protein

<400> SEQUENCE: 1
atgaacctgg gtctggattg tgacgagcac tcttctgaaa gccgttgttg ccgttaccct      60
ctgactgtag acttcgaagc attcggttgg gactggatca tcgctccaaa acgctacaag     120
gcgaactact gcagcggtca atgtgaatac atgtttatgc agaaataccc gcacacccat     180
ctggtccagc aggccaaccc gcgtggttcc gcgggcccgt gttgcacgcc gaccaaaatg     240
tctcgattaa catgctgtat ttcaatgata aacagcagat catctatggc aaaattccgg     300
gcatggtggt tgatcgctgc ggctgctaac tcagactctg agtgcccact gtctcacgac     360
ggctactgcc ttcacgacgg agtctgcatg tacatcgagg ctttggataa gtacgcttgt     420
aattgcgtcg ttggttacat tggagagcgc tgccaatacc gtgacttaaa atggtgggag     480
ttgcgc                                                                486

<210> SEQ ID NO 2
<211> LENGTH: 162
<212> TYPE: PRT
<213> ORGANISM: Artificial Sequence
<220> FEATURE:
<223> OTHER INFORMATION: GDF11-EGF fusion protein

<400> SEQUENCE: 2

Met Asn Leu Gly Leu Asp Cys Asp Glu His Ser Ser Glu Ser Arg Cys
1               5                   10                  15

Cys Arg Tyr Pro Leu Thr Val Asp Phe Glu Ala Phe Gly Trp Asp Trp
            20                  25                  30

Ile Ile Ala Pro Lys Arg Tyr Lys Ala Asn Tyr Cys Ser Gly Gln Cys
        35                  40                  45

Glu Tyr Met Phe Met Gln Lys Tyr Pro His Thr His Leu Val Gln Gln
    50                  55                  60

Ala Asn Pro Arg Gly Ser Ala Gly Pro Cys Cys Thr Pro Thr Lys Met
65                  70                  75                  80

Ser Arg Leu Thr Cys Cys Ile Ser Met Ile Asn Ser Arg Ser Ser Met
                85                  90                  95

Ala Lys Phe Arg Ala Trp Trp Leu Ile Ala Ala Ala Asn Ser Asp
                100                 105                 110

Ser Glu Cys Pro Leu Ser His Asp Gly Tyr Cys Leu His Asp Gly Val
            115                 120                 125
```

Cys Met Tyr Ile Glu Ala Leu Asp Lys Tyr Ala Cys Asn Cys Val Val
            130                 135                 140

Gly Tyr Ile Gly Glu Arg Cys Gln Tyr Arg Asp Leu Lys Trp Trp Glu
145                 150                 155                 160

Leu Arg

<210> SEQ ID NO 3
<211> LENGTH: 486
<212> TYPE: DNA
<213> ORGANISM: Artificial Sequence
<220> FEATURE:
<223> OTHER INFORMATION: EGF-GDF11 fusion protein

<400> SEQUENCE: 3
atgaactcag actctgagtg cccactgtct cacgacggct actgccttca cgacggagtc    60
tgcatgtaca tcgaggcttt ggataagtac gcttgtaatt gcgtcgttgg ttacattgga   120
gagcgctgcc aataccgtga cttaaaatgg tgggagttgc gcaacctggg tctggattgt   180
gacgagcact cttctgaaag ccgttgttgc cgttaccctc tgactgtaga cttcgaagca   240
ttcggttggg actggatcat cgctccaaaa cgctacaagg cgaactactg cagcggtcaa   300
tgtgaataca tgtttatgca gaaatacccg cacacccatc tggtccagca ggccaacccg   360
cgtggttccg cgggcccgtg ttgcacgccg accaaaatgt ctcgattaac atgctgtatt   420
tcaatgataa acagcagatc atctatggca aaattccggg catggtggtt gatcgctgcg   480
gctgct                                                              486

<210> SEQ ID NO 4
<211> LENGTH: 162
<212> TYPE: PRT
<213> ORGANISM: Artificial Sequence
<220> FEATURE:
<223> OTHER INFORMATION: EGF-GDF11 fusion protein

<400> SEQUENCE: 4

Met Asn Ser Asp Ser Glu Cys Pro Leu Ser His Asp Gly Tyr Cys Leu
1               5                   10                  15

His Asp Gly Val Cys Met Tyr Ile Glu Ala Leu Asp Lys Tyr Ala Cys
            20                  25                  30

Asn Cys Val Val Gly Tyr Ile Gly Glu Arg Cys Gln Tyr Arg Asp Leu
        35                  40                  45

Lys Trp Trp Glu Leu Arg Asn Leu Gly Leu Asp Cys Asp Glu His Ser
    50                  55                  60

Ser Glu Ser Arg Cys Cys Arg Tyr Pro Leu Thr Val Asp Phe Glu Ala
65                  70                  75                  80

Phe Gly Trp Asp Trp Ile Ile Ala Pro Lys Arg Tyr Lys Ala Asn Tyr
                85                  90                  95

Cys Ser Gly Gln Cys Glu Tyr Met Phe Met Gln Lys Tyr Pro His Thr
            100                 105                 110

His Leu Val Gln Gln Ala Asn Pro Arg Gly Ser Ala Gly Pro Cys Cys
        115                 120                 125

Thr Pro Thr Lys Met Ser Arg Leu Thr Cys Cys Ile Ser Met Ile Asn
    130                 135                 140

Ser Arg Ser Ser Met Ala Lys Phe Arg Ala Trp Trp Leu Ile Ala Ala
145                 150                 155                 160

Ala Ala

```
<210> SEQ ID NO 5
<211> LENGTH: 17
<212> TYPE: DNA
<213> ORGANISM: Artificial Sequence
<220> FEATURE:
<223> OTHER INFORMATION: primer

<400> SEQUENCE: 5
catatgaacc tgggtct                                                 17

<210> SEQ ID NO 6
<211> LENGTH: 15
<212> TYPE: DNA
<213> ORGANISM: Artificial Sequence
<220> FEATURE:
<223> OTHER INFORMATION: primer

<400> SEQUENCE: 6
ctcgaggcgc aactc                                                   15

<210> SEQ ID NO 7
<211> LENGTH: 18
<212> TYPE: DNA
<213> ORGANISM: Artificial Sequence
<220> FEATURE:
<223> OTHER INFORMATION: primer

<400> SEQUENCE: 7
catatgaact cagactct                                                18

<210> SEQ ID NO 8
<211> LENGTH: 18
<212> TYPE: DNA
<213> ORGANISM: Artificial Sequence
<220> FEATURE:
<223> OTHER INFORMATION: primer

<400> SEQUENCE: 8
ctcgagagca gccgcagc                                                18
```

FUSION PROTEIN COMPRISING GROWTH DIFFERENTIATION FACTOR 11 AND EPIDERMAL GROWTH FACTOR WITH ENHANCED ANTI-OXIDATION ACTIVITY AND ENHANCED SKIN CELL PROLIFERATION EFFECT AND COSMETIC COMPOSITION FOR ANTI-WRINKLE COMPRISING THE SAME AS EFFECTIVE COMPONENT

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2017/005751, filed Jun. 1, 2017, which claims priority to the benefit of Korean Patent Application No. 10-2017-0065257 filed in the Korean Intellectual Property Office on May 26, 2017, the entire contents of which are incorporated herein by reference.

BACKGROUND

1. Technical Field

The present invention relates to a fusion protein comprising growth differentiation factor 11 and epidermal growth factor with enhanced anti-oxidation activity and enhanced skin cell proliferation effect and an anti-wrinkle cosmetic composition comprising the fusion protein as effective component.

2. Background Art

It is known that various growth factors are involved in growth, proliferation, differentiation of cells, and those growth factors are characterized in that they exhibit their respective functions upon binding to a specific receptor. Due to the short half-life and insufficient stability, it remains difficult to produce those growth factors on a large scale. However, thanks to the progress in genetic recombination techniques, now it becomes possible to overcome the problem.

In 2013, Prof. Amy Wagers of Harvard University (U.S.A) discovered growth differentiation factor 11 (GDF 11) that is closely related to anti-aging. Based on the result indicating that senile rats can recover their youth through parabiosis between them and young rats, she published in 2014 a research paper relating to the anti-aging activity of growth differentiation factor 11. However, researchers of Novartis Biomedical Research Institute opposed the anti-aging effect of growth differentiation factor 11, by focusing on the fact that the amino acid sequence of myostatin, which inhibits muscle growth, is very similar to the amino acid sequence of growth differentiation factor 11. Although the debate is still ongoing, growth differentiation factor 11 is known to be a protein which promotes regeneration and elasticity of skin like fibroblast, collagen, and elastin.

Rapid progress in cosmetic industry leads to the development of new materials for cosmetic products, and, currently, the development of techniques for developing new materials and high-functional cosmetics is continuously made over the entire cosmetic industry. In particular, human epidermal growth factor (hEGF) is one of those materials which receive considerable attention of the consumers as it has an excellent skin regeneration effect including wrinkle improvement, skin whitening, and the like.

Upon binding to an epidermal growth factor receptor that is present on a cell surface, hEGF induces dimerization of the epidermal growth factor receptor. The epidermal growth factor receptor as a dimer activates the tyrosine kinase present inside the receptor so that the intracellular signal transduction system is activated. Based on this process, glycolysis and protein synthesis are promoted in the cell, which finally leads to cell growth. The epidermal growth factor playing a key role in skin regeneration is reduced with aging, and reduced epidermal growth factor causes less proliferation and less movement of skin cells, consequently yielding phenomena like skin aging, excessive wrinkles, reduced skin elasticity, or the like.

In the present invention, a fusion protein having an excellent skin regeneration effect is developed according to fusion between growth differentiation factor 11 and epidermal growth factor, and a cosmetic composition for regenerating skin and improving skin wrinkle which comprises the fusion protein as effective component is also developed.

Meanwhile, in Korean Patent Registration No. 1609041, "Cosmetic composition for skin improvement comprising fusion protein of epidermal growth factor" is disclosed, and, in Korean Patent Application Publication No. 2013-0138563, "Composition for preventing aging comprising photosensitive chitosan derivatives and epidermal growth factor immobilized thereto" is disclosed. However, the fusion protein comprising growth differentiation factor 11 and epidermal growth factor with enhanced anti-oxidation activity and enhanced skin cell proliferation effect and an anti-wrinkle cosmetic composition comprising the fusion protein as effective component are not disclosed before.

SUMMARY

The present invention is devised under the circumstances that are described in the above, and the inventors of the present invention prepared a novel fusion protein according to fusion between a gene encoding growth differentiation factor 11 and a gene encoding human epidermal growth factor, in which the genes are *Escherichia coli* (*E. coli*) codon-optimized. It was also found that, as a result of treating a skin cell line with the fusion protein comprising growth differentiation factor 11 and epidermal growth factor as prepared, a more excellent anti-oxidation effect is obtained from a treatment with the fusion protein compared to a treatment with the individual proteins, and also a more excellent cell proliferation effect is obtained from a treatment with the fusion protein compared to a treatment with the individual proteins, thus the present invention is completed accordingly.

To solve the problems that are described in the above, the present invention provides a fusion protein comprising growth differentiation factor 11 and epidermal growth factor with enhanced anti-oxidation activity and enhanced skin cell proliferation effect in which the fusion protein consists of the amino acid sequence of SEQ ID NO: 2 or SEQ ID NO: 4.

The present invention further provides a gene encoding the aforementioned fusion protein.

The present invention further provides a recombinant vector comprising the aforementioned gene.

The present invention further provides a host cell transformed with the aforementioned recombinant vector.

The present invention further provides a method for producing in a host cell a fusion protein comprising growth differentiation factor 11 and epidermal growth factor including transforming a host cell with the aforementioned recombinant vector.

The present invention further provides a fusion protein comprising growth differentiation factor 11 and epidermal growth factor produced by the aforementioned method.

The present invention still further provides a cosmetic composition for regenerating skin and improving skin wrinkle comprising, as an effective component, a fusion protein comprising growth differentiation factor 11 and epidermal growth factor in which the fusion protein consists of the amino acid sequence of SEQ ID NO: 2 or SEQ ID NO: 4.

The production method of the present invention, in which the production in *E. coli* is made by using a gene encoding the fusion protein comprising growth differentiation factor 11 and epidermal growth factor in which the gene is *E. coli* codon-optimized, enables a simplified production process as the recombinant protein is expressed in form of an inclusion body in *E. coli*, and the method also enables production of the recombinant protein in large amount. Furthermore, the fusion protein comprising growth differentiation factor 11 and epidermal growth factor which is produced by the aforementioned method has an excellent anti-oxidation effect and an excellent skin regeneration effect, and thus it is expected that the fusion protein can be advantageously used as a raw material of novel functional cosmetics for skin whitening, anti-aging, or wrinkle improvement.

DETAILED DESCRIPTION

Figure 1:
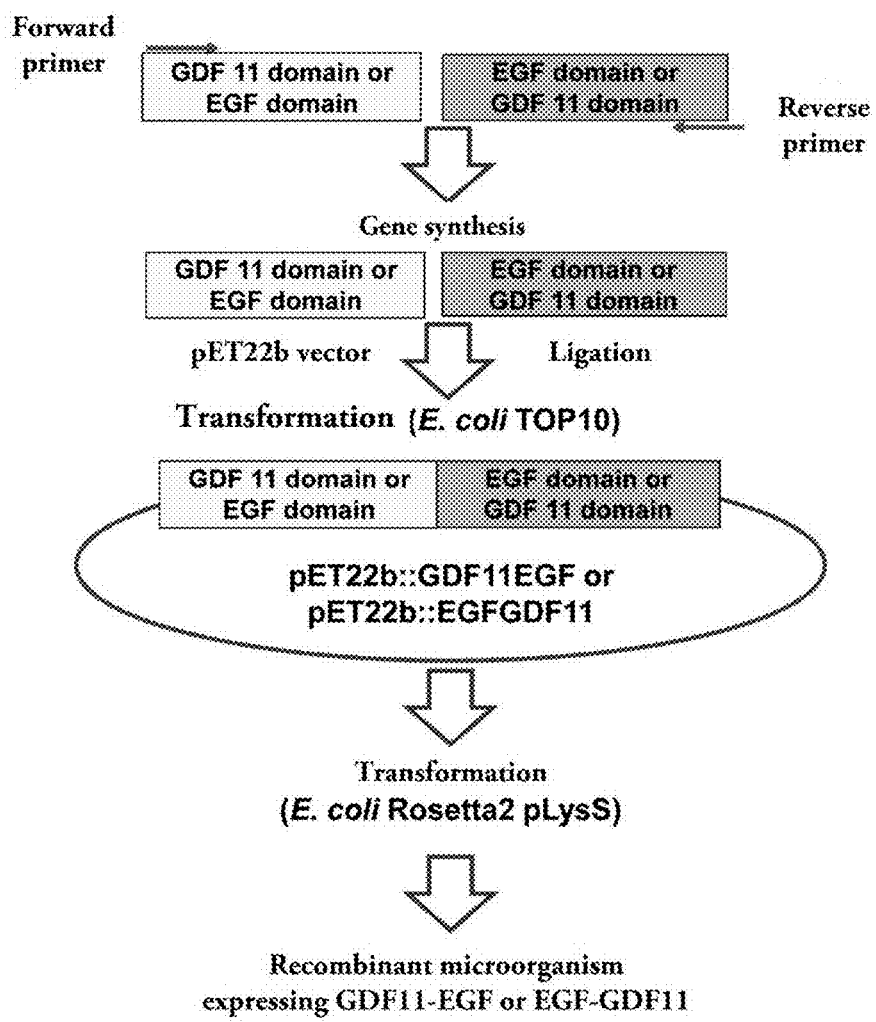
FIG. 1 is a schematic drawing illustrating the process of producing the recombinant plasmid (pET22b::GDF11EGF and pET22b::EGFGDF11) which contains a gene encoding the fusion protein comprising growth differentiation factor 11 (GDF11) and epidermal growth factor (EGF), and transformation of *E. coli* with the recombinant plasmid.

To achieve the object of the present invention, the present invention provides a fusion protein comprising growth differentiation factor 11 and epidermal growth factor with enhanced anti-oxidation activity and enhanced skin cell proliferation effect in which the fusion protein consists of the amino acid sequence of SEQ ID NO: 2 or SEQ ID NO: 4.

A protein having the amino acid sequence represented by SEQ ID NO: 2 (human epidermal growth factor is fused to the carboxy terminal of growth differentiation factor 11) or SEQ ID NO: 4 (human epidermal growth factor is fused to the amino terminal of growth differentiation factor 11) and also functional equivalents of the protein fall within the scope of the fusion protein comprising growth differentiation factor 11 and epidermal growth factor according to the present invention. The term "functional equivalents" indicates a protein having, as a result of addition, substitution, or deletion of an amino acid, at least 70%, preferably at least 80%, more preferably at least 90%, and even more preferably at least 95% sequence homology with the amino acid sequence represented by SEQ ID NO: 2 or SEQ ID NO: 4, and it indicates a protein exhibiting substantially the same activity as the protein represented by SEQ ID NO: 2 or SEQ ID NO: 4. The expression "substantially the same activity" means an anti-oxidation activity and a skin regeneration activity. Also included in the present invention are fragments, derivatives, and analogues of the fusion protein comprising growth differentiation factor 11 and epidermal growth factor. The terms "fragments", "derivatives", and "analogues" that are described in the present specification indicate a polypeptide with the substantially same biological function or activity as the fusion protein comprising growth differentiation factor 11 and epidermal growth factor of the present invention.

The fusion protein comprising growth differentiation factor 11 and epidermal growth factor of the present invention preferably consists of the amino acid sequence of SEQ ID NO: 2 or SEQ ID NO: 4, and the fusion protein consisting of the amino acid sequence of SEQ ID NO: 2 is a novel protein that is produced by fusion between the growth differentiation factor 11 consisting of the $1^{st}$ to the $109^{th}$ amino acids of the amino acid sequence of SEQ ID NO: 2 and human epidermal growth factor consisting of the $110^{th}$ to the $162^{nd}$ amino acids of the amino acid sequence of SEQ ID NO: 2. In addition, the fusion protein consisting of the amino acid sequence of SEQ ID NO: 4 is a novel protein that is produced by fusion between the human epidermal growth factor consisting of the $2^{nd}$ to the $54^{th}$ amino acids of the amino acid sequence of SEQ ID NO: 4 and growth differentiation factor 11 consisting of the $55^{th}$ to the $162^{nd}$ amino acids of the amino acid sequence of SEQ ID NO: 4.

The present invention further provides a gene encoding the fusion protein comprising growth differentiation factor 11 and epidermal growth factor which has an enhanced anti-oxidation activity and an enhanced skin cell proliferation effect. The gene may consist of the *E. coli* codon-optimized nucleotide sequence of SEQ ID NO: 1 or SEQ ID NO: 3, but it is not limited thereto.

This gene encoding the fusion protein comprising growth differentiation factor 11 and epidermal growth factor with enhanced anti-oxidation activity and enhanced skin cell proliferation effect of the present invention may include the nucleotide sequence of SEQ ID NO: 1 (i.e., gene encoding a protein in which human epidermal growth factor is fused to the carboxy terminal of growth differentiation factor 11) or SEQ ID NO: 3 (i.e., gene encoding a protein in which human epidermal growth factor is fused to the amino terminal of growth differentiation factor 11). Furthermore, homologues of the nucleotide sequence are also within the scope of the present invention. Specifically, the above described gene may comprise a nucleotide sequence which has preferably at least 70%, more preferably at least 80%, still more preferably at least 90%, and most preferably at least 95% homology with the nucleotide sequence selected from a group consisting of nucleotide sequences of SEQ ID NO: 1 or SEQ ID NO: 3. The "sequence homology %" for a certain polynucleotide is identified by comparing a comparative region with two sequences that are optimally aligned. In this regard, a part of the polynucleotide in comparative region may comprise an addition or a deletion (i.e., a gap) compared to a reference sequence (without any addition or deletion) relative to the optimized alignment of the two sequences.

"Codon-optimized" means a modification of codon of a polynucleotide encoding a protein with a codon that is used first than others in a specific organism such that the coded protein can be more efficiently expressed therein. Because most amino acids are described by several codons that are referred to as "synonym" or "synonymous codon", genetic codes have degeneracy. However, codon usage by a specific organism is not random, and it is rather biased to specific codon triplets. Such codon usage bias may be even higher in relation with a certain gene, a gene with common function or ancestor origin, protein expressed at high level vs. proteins with low copy number, or a group protein coding region of a genome of an organism. The nucleotide sequence of SEQ ID NO: 1 or SEQ ID NO: 3 of the present invention is a sequence which has been optimized to *E. coli* codon such that the gene encoding the fusion protein comprising growth differentiation factor 11 and epidermal growth factor can be expressed in *E. coli*.

The present invention further provides a recombinant vector comprising the aforementioned gene, and a host cell transformed with the recombinant vector.

The term "recombinant" indicates a cell which replicates a heterogeneous nucleotide or expresses said nucleotide, or a peptide, a heterogeneous peptide, or a protein encoded by a heterogeneous nucleotide. Recombinant cell can express a gene or a gene fragment in the form of a sense or antisense, which are not found in natural state of cell. In addition, a recombinant cell can express a gene that is found in natural state, provided that said gene is modified and re-introduced into the cell by an artificial means.

According to the present invention, the gene encoding a fusion protein comprising growth differentiation factor 11 and epidermal growth factor can be inserted to a recombinant expression vector. The term "recombinant expression vector" means bacteria plasmid, phage, yeast plasmid, plant cell virus, mammalian cell virus, or other vector. In general, any plasmid and vector can be used if it can replicate and be stabilized in a host. Important characteristics of the expression vector include that it comprises a replication origin, a promoter, a marker gene, and a translation control element.

The expression vector comprising the gene sequence encoding a fusion protein comprising growth differentiation factor 11 and epidermal growth factor and an appropriate signal for regulating transcription/translation can be constructed according to a method that is well known to a skilled person in the art. The method includes an in vitro recombinant DNA technique, a DNA synthesis technique, and an in vivo recombinant technique. For inducing mRNA synthesis, the DNA sequence can be effectively linked to a suitable promoter present in the expression vector. In addition, the expression vector may comprise a ribosome binding site as a translation initiation site and a transcription terminator.

The recombinant vector according to one embodiment of the present invention is prepared by in-frame fusion of a synthesized gene encoding the fusion protein comprising growth differentiation factor 11 and epidermal growth factor (i.e., SEQ ID NO: 1 or SEQ ID NO: 3) at 5' terminus (NdeI restriction enzyme site) and 3' terminus (XhoI restriction enzyme site) in pET22b vector, and the recombinant vector may be a recombinant vector characterized in that it can produce the fusion protein comprising growth differentiation factor 11 and epidermal growth factor based on effective expression of the aforementioned gene with an aid of lac promoter (lac promoter) and lad repressor (lad repressor), but it is not limited thereto.

As a host cell having an ability of having stable and continuous cloning and expression of the vector of the present invention in a prokaryotic cell, any host cell known in the pertinent art can be used. Examples of the prokaryotic cells include, *Bacillus* sp. strain including *E. coli* Rosetta, *E. coli* JM109, *E. coli* BL21, *E. coli* RR1, *E. coli* LE392, *E. coli* B, *E. coli* X 1776, *E. coli* W3110, *Bacillus subtillus, Bacillus thuringiensis* and the like, and intestinal bacteria and strains including *Salmonella typhimurium, Serratia marcescens* and various *Pseudomonas* sp. etc.

Furthermore, when a eukaryotic cell is transformed with the vector of the present invention, yeast (*Saccharomyces cerevisiae*), an insect cell, a human cell (for example, CHO (Chinese hamster ovary) cell line, W138, BHK, COS-7, HEK 293, HepG2, 3T3, RIN, and MDCK cell line), a plant cell, and the like can be used as a host cell.

The transformed host cell of the present invention may be *E. coli* Rosetta2 (DE3) pLysS cell line, but it is not limited thereto.

When a host cell is a prokaryotic cell, delivery of the vector of the present invention into a host cell can be carried out by $CaCl_2$ method, Hanahan's method (Hanahan, D., *J. Mol. Biol.,* 166:557-580 (1983)) or an electroporation method, and the like. In addition, when a host cell is a eukaryotic cell, the vector can be introduced to a host cell by a microinjection method, calcium phosphate precipitation method, an electroporation method, a liposome-mediated transfection method, DEAE-dextran treatment method, or a gene bombardment method, and the like.

The present invention further provides a method for producing in a host cell a fusion protein comprising growth differentiation factor 11 and epidermal growth factor including transforming a host cell with the aforementioned recombinant vector to overexpress a gene encoding the fusion protein comprising growth differentiation factor 11 and epidermal growth factor, and the invention also provides a fusion protein comprising growth differentiation factor 11 and epidermal growth factor that is produced by the aforementioned method.

In the method according to one embodiment of the present invention, the host cell may be preferably *E. coli*, and more preferably *E. coli* Rosetta2 (DE3) pLysS cell line, but it is not limited thereto.

The present invention still further provides a cosmetic composition for regenerating skin and improving skin wrinkle comprising, as an effective component, a fusion protein comprising growth differentiation factor 11 and epidermal growth factor in which the fusion protein consists of the amino acid sequence of SEQ ID NO: 2 or SEQ ID NO: 4.

In the cosmetic composition according to one embodiment of the present invention, content of the fusion protein comprising growth differentiation factor 11 and epidermal growth factor may be 0.000001 to 0.00002% by weight relative to the total weight of the cosmetic composition, but it is not limited thereto.

In the cosmetic composition of the present invention, components that are typically used for a cosmetic composition are included in addition to the effective component described above. Examples thereof include a lipid material, an organic solvent, a dissolution agent, a condensation agent, a gelling agent, a softening agent, an anti-oxidant, a suspension agent, a stabilizer, a foaming agent, an aroma, a surface active agent, water, an ionic or non-ionic emulsifier, a filler, a metal ion sequestering agent, a chelating agent, a preservative, vitamin, a blocking agent, a moisturizing agent, essential oil, a dye, a pigment, a hydrophilic or lipophilic activating agent, a common auxiliary agent such as lipid vesicle, and a carrier.

The composition of the present invention can be prepared in any formulation which is generally prepared in the pertinent art. For example, the composition may be formulated into a solution, a suspension, an emulsion, a paste, a gel, a crème, a lotion, a powder, an oil, a powder foundation, an emulsion foundation, a wax foundation, a spray, or the like, but not limited thereto. More specifically, the composition may be formulated into a skin, a skin softener, a skin toner, an astringent, a lotion, a milk lotion, a moisture lotion, a nutrition lotion, a massage crème, a nutrition crème, an eye crème, a moisture crème, a hand crème, an essence, a nutrition essence, a pack, a cleansing foam, a cleansing water, a cleansing lotion, a cleansing crème, a body lotion, a body cleanser, a soap, a powder, or the like.

In a case in which the cosmetic composition of the present invention has a formulation type of paste, crème, or gel, it is possible to use, as a carrier component, animal oil, plant oil, wax, paraffin, starch, tragacanth, cellulose derivatives, polyethylene glycol, silicone, bentonite, silica, talc, or zinc oxide.

In a case in which the cosmetic composition of the present invention has a formulation type of powder or spray, it is possible to use, as a carrier component, lactose, talc, silica, aluminum hydroxide, calcium silicate, or polyamide powder, when it is spray, in particular, a propellant such as chlorofluoro hydrocarbon, propane/butane, or dimethyl ether may be additionally contained.

In a case in which the cosmetic composition of the present invention has a formulation type of solution or emulsion, a solvent, a dissolution agent, or an emulsifier is used as a carrier component, and examples thereof include water, ethanol, isopropyl alcohol, ethyl carbonate, ethyl acetate, benzyl alcohol, benzyl benzoate, propylene glycol, 1,3-butyl glycol oil, glycerol aliphatic ester, polyethylene glycol, and fatty acid ester of sorbitan.

In a case in which the cosmetic composition of the present invention has a formulation type of suspension, it is possible to use, as a carrier component, a liquid phase diluent such as water, ethanol, or propylene glycol, a suspension agent such as ethoxylated isostearyl alcohol, polyoxyethlyene sorbitol ester, or polyoxyethylene sorbitan ester, microcrystalline cellulose, aluminum metahydroxide, bentonite, agar, or tragacanth.

Hereinbelow, the present invention is explained in greater detail in view of the Examples. However, it is evident that the following Examples are given only for exemplification of the present invention and by no means the present invention is limited to the following Examples.

EXAMPLES

Example 1. Preparation of Recombinant Expression Vector and Transformed Recombinant Microorganism for Producing Fusion Protein Comprising Growth Differentiation Factor 11 and Human Epidermal Growth Factor The optimized gene encoding the fusion protein comprising growth differentiation factor 11 and epidermal growth factor of the present invention, recombinant expression vector, and transformed recombinant microorganism were produced according to the methods that are described below.

By using as a template a gene encoding growth differentiation factor 11 and a gene encoding human epidermal growth factor, which is used as a partner protein, a gene (SEQ ID NO: 1 or SEQ ID NO: 3) fragment encoding a fusion protein comprising growth differentiation factor 11 and epidermal growth factor, which consists of 162 amino acids and is optimized such that it can be expressed in a host microorganism, was synthetically prepared.

To synthesize a gene encoding the fusion protein (SEQ ID NO: 2) comprising growth differentiation factor 11 and epidermal growth factor in which human epidermal growth factor is linked to the carboxy terminal (C-terminus) of growth differentiation factor 11, by using forward primer 1 (5'-CATATGAACCTGGGTCT-3; SEQ ID NO: 5) and reverse primer 1 (5'-CTCGAGGCGCAACTC-3'; SEQ ID NO: 6), a gene consisting of 486 nucleotides which encodes the fusion protein having 327 nucleotides (i.e., $1^{st}$ to $327^{th}$ nucleotide sequence of SEQ ID NO: 1) encoding E. coli-optimized growth differentiation factor 11 and 159 nucleotides (i.e., $328^{th}$ to $486^{th}$ nucleotide sequence of SEQ ID NO: 1) encoding E. coli-optimized human epidermal growth factor was synthesized by polymerase chain reaction (PCR).

To synthesize a gene encoding the fusion protein (SEQ ID NO: 4) comprising growth differentiation factor 11 and human epidermal growth factor in which human epidermal growth factor is linked to the amino terminal (N-terminus) of growth differentiation factor 11, by using forward primer 1 (5'-CATATGAACCTGGGTCT-3'; SEQ ID NO: 7) and reverse primer 1 (5'-CTCGAGAGCAGCCGCAGC-3; SEQ ID NO: 8), a gene encoding the fusion protein having human epidermal growth factor linked to the amino terminal of growth differentiation factor 11 was synthesized in the same manner as above.

According to digestion of the above gene fragment and recombinant plasmid with the same restriction enzymes (5' terminus NdeI and 3' terminus XhoI) followed by insertion, the recombinant plasmid (pET22b::GDF11EGF and pET22b::EGFGDF11) shown in FIG. 1 was prepared. By transforming E. coli TOP10 with the prepared recombinant plasmid, the gene construct was obtained in large amount from the host microorganism.

After that, E. coli Rosetta2 (DE3) pLysS (Novagen, Germany) was transformed with the prepared recombinant plasmid so that a recombinant microorganism for producing the fusion protein comprising growth differentiation factor 11 and epidermal growth factor was prepared.

Example 2. Induced Expression, Separation, and Purification of Fusion Protein Comprising Growth Differentiation Factor 11 and Human Epidermal Growth Factor E. coli Rosetta2 (DE3) pLysS prepared in Example 1 was cultured by using 1 l LB medium (10% tryptophan, 10% sodium chloride, and 5% yeast extract) or BSS medium (1% tryptophan, 0.5% yeast extract, 1% glucose, and 0.1% HEPES (pH 7.0), Nexgen Biotechnologies, Inc.) till to have $OD_{600}$=0.6 to 0.8 for batch culture, or $OD_{600}$=15 to 20 for continuous culture which uses a 20 l fermenter. After that, by adding 1 to 5 mM IPTG or 2% lactose (each at final concentration) to the cell culture medium, gene expression of the recombinant E. coli was induced. After inducing the gene expression, the cells were additionally cultured for 3 to 4 hours, and then collected by centrifuge. The resulting cells were completely suspended in phosphate buffered saline (8 g sodium chloride, 0.2 g potassium chloride, 1.44 g sodium hydrogen phosphate ($Na_2HPO_4$), and 0.24 g potassium dihydrogen phosphate (KH$_2$PO$_4$)/f, pH 7.4), and then disrupted by using an ultrasonic homogenizer so as to separate a solution containing the intracellular proteins. By using thus-separated solutions as a sample, protein expression was determined by 15% SDS-polyacrylamide gel electrophoresis. As a result, it was found that the fusion protein comprising growth differentiation factor 11 and epidermal growth factor is expressed in a crude lysate of cells which have been induced by IPTG or lactose to undergo the expression.

In order to separate and purify the fusion protein comprising growth differentiation factor 11 and epidermal growth factor of which expression has been confirmed, the inclusion body was solubilized with a solubilizing buffer solution (5 M urea, pH 11), and then subjected to a refolding process by ultrafine filtration (0.45 μm fine filtration membrane and 1 K ultrafine filtration membrane). By using a buffer solution for storage (PBS), the fusion protein comprising growth differentiation factor 11 and epidermal growth factor was finally separated.

Figure 2:
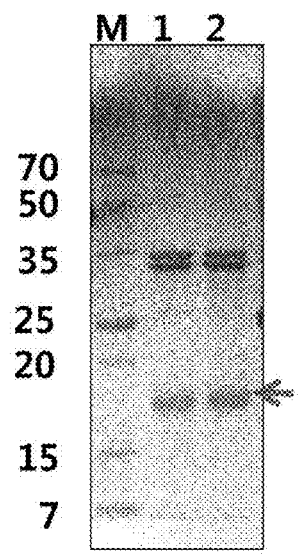
FIG. 2 shows the photographic image of SDS-PAGE gel of a fusion protein which has been finally separated and purified after the expression of the fusion protein of the present invention in *E. coli*, in which M represents a size marker; 1 represents a fusion protein comprising growth differentiation factor 11 and epidermal growth factor (GDF11-EGF), and; 2 represents a fusion protein comprising epidermal growth factor and growth differentiation factor 11 (EGF-GDF11).

For having complete purification of the above fusion protein, the separated fusion protein was passed through a nickel-agarose column at a rate of 1 to 3 ml/minute. Subsequently, the column was washed several times with a binding buffer solution, and an imidazole solution (pH 7.4) at a concentration of 50, 100, or 250 mM was applied to the column to fractionate and elute the fusion protein comprising growth differentiation factor 11 and epidermal growth factor, in which each fraction is eluted in an amount of 1 ml. Then, the imidazole in the buffer was removed by using 10 mM potassium phosphate solution so that the fusion protein was finally purified in pure state. To examine the result, 15% SDS-polyacrylamide gel electrophoresis was carried out. As a result, the finally purified fusion protein was found near the region having the expected size (about 17 kDa including His tag) (FIG. 2).

Example 3. Activity Measurement of Fusion Protein Comprising Growth Differentiation Factor 11 and Epidermal Growth Factor: Dermal Fibroblast Cell Proliferation Effect After selecting samples from which the presence of the fusion protein comprising growth differentiation factor 11 and epidermal growth factor has been confirmed as the fusion protein is separated and purified in Example 2, activity of the fusion protein was measured.

Dermal fibroblast cells (Human Dermal Fibroblasts adult, HDFa cell) were cultured, and then treated, at a concentration of 0, 0.02, 0.2, 2.0, or 20 ppm, with active domain of growth differentiation factor 11 (GDF11) which has been used for producing the fusion protein, or with the fusion protein comprising growth differentiation factor 11 and epidermal growth factor followed by culture for 3 days at 37° C. After that, proliferation of the dermal fibroblast cells was examined by crystal violet staining.

Figure 3:
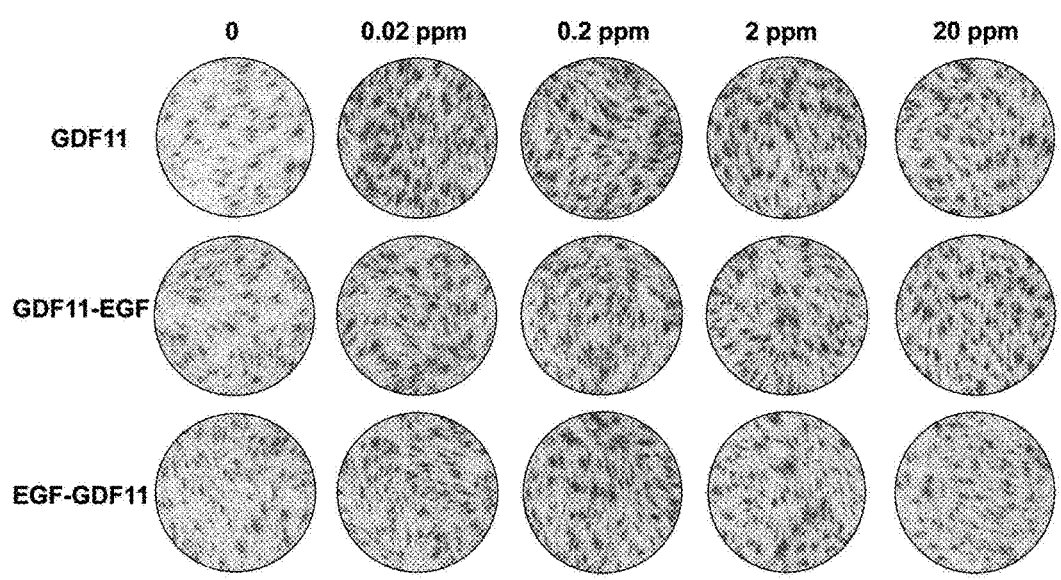
FIG. 3 shows the result of determining the cell proliferation of dermal fibroblast cells after treating the cells with growth differentiation factor 11 (GDF11) only, or with a fusion protein comprising growth differentiation factor 11 and epidermal growth factor (GDF11-EGF, EGF-GDF11), in which the determination was made based on crystal violet staining after the treatment.

As a result, it was found that a more excellent dermal fibroblast proliferation effect is obtained as the concentration of the fusion protein comprising growth differentiation factor 11 and epidermal growth factor increases (FIG. 3). It was also observed that the cell proliferation effect exhibited by the fusion protein comprising growth differentiation factor 11 and epidermal growth factor (i.e., GDF11-EGF, EGF-GDF11) is similar to the effect of the group treated with single protein (i.e., active domain of GDF11). In this regard, instead of being a full-length protein, each of growth differentiation factor 11 domain and epidermal growth factor domain in the fusion protein corresponds to the separate active domain that has been used for producing the fusion protein of the present invention, and, when the treatment is carried out with single protein or the fusion protein at same concentration (e.g., 0.2 ppm), mole number of the fusion protein would be about ½ of the mole number of single protein (i.e., active domain of GDF11). As such, if a similar dermal fibroblast proliferation effect is shown at the same concentration, the fusion protein is recognized to have a dermal fibroblast proliferation effect that is about 2 times higher than the proliferation effect of single protein (i.e., active domain of GDF11). As it can be seen from FIG. 3, since the dermal fibroblast proliferation effect obtained by a treatment with the fusion protein comprising growth differentiation factor 11 and epidermal growth factor is similar to the effect of GDF11 active domain only, it is found that the dermal fibroblast proliferation effect of the fusion protein is at least 2 times higher than the treatment with active domain of growth differentiation factor 11. Based on this result, it was found that the fusion protein comprising growth differentiation factor 11 and epidermal growth factor according to the present invention has an excellent skin cell proliferation effect.

Example 4. Activity Measurement of Fusion Protein Comprising Growth Differentiation Factor 11 and Epidermal Growth Factor: Anti-Oxidation Effect In order to examine the anti-oxidation activity of the fusion protein comprising growth differentiation factor 11 and epidermal growth factor, DPPH (1,1-diphenyl-2-pycrylhydrazyl) method, which is one of the methods for measuring the free radical scavenging activity, was used.

Figure 4:
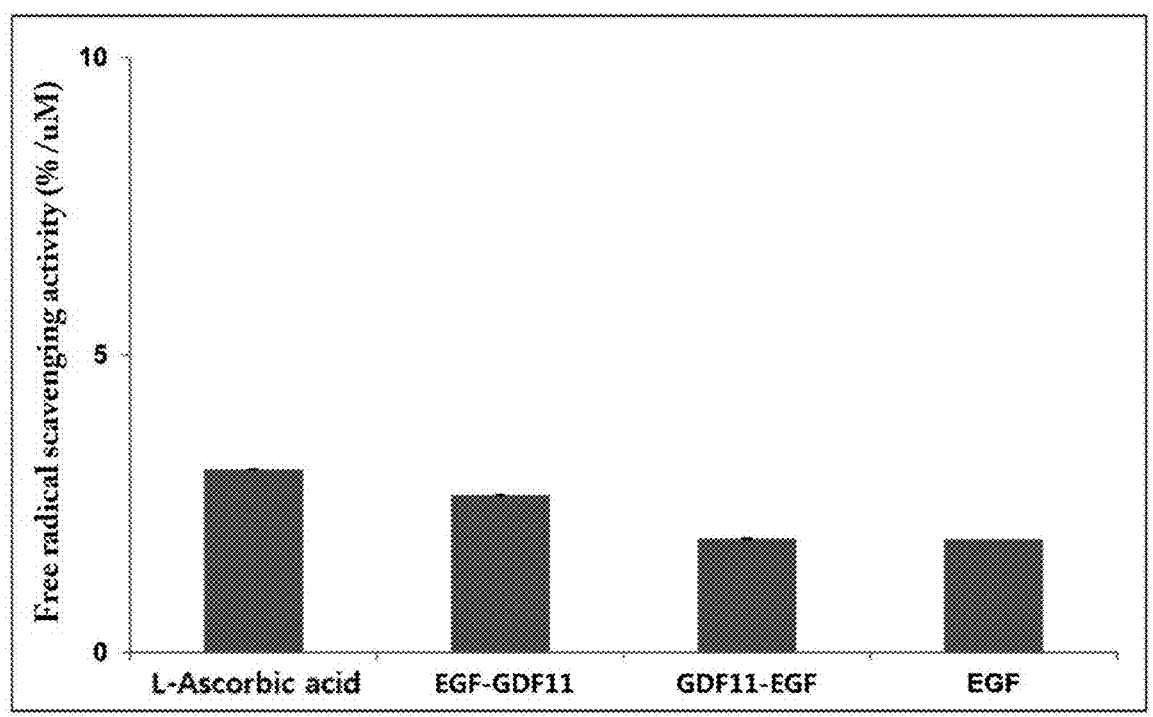
FIG. 4 shows the result of determining the anti-oxidation activity of the fusion protein comprising growth differentiation factor 11 and epidermal growth factor.

In order to examine the anti-oxidation activity of the fusion protein comprising growth differentiation factor 11 and epidermal growth factor, L-ascorbic acid was used as a control group. For the test, epidermal growth factor, a fusion protein comprising growth differentiation factor 11 and epidermal growth factor (EGF-GDF11, GDF11-EGF), and L-ascorbic acid were prepared each at 1 μM concentration while DPPH was prepared at concentration of 0.2 mM. After mixing each of them at a ratio of 1:1, they were allowed to stand for 30 minutes at 37° C. After that, the absorbance at 520 nm was measured by using an ELISA reader. The free radical scavenging activity (%) was calculated based on the following equation 1, and the results are shown in FIG. 4.

Free radical scavenging activity (%)=100−(($B/A$)*100)   [Equation 1]

A: Absorbance by control group which has not been treated with any test sample

B: Absorbance by test group which has been treated with test sample

As a result, it was shown that the fusion protein comprising growth differentiation factor 11 and epidermal growth factor showed slightly lower free radical scavenging activity than L-ascorbic acid as a positive control group. However, the free radical scavenging activity of the fusion protein comprising epidermal growth factor and growth differentiation factor 11 (EGF-GDF11) was higher than the activity of the group which has been treated only with epidermal growth factor protein (FIG. 4). It was also observed that the free radical scavenging activity exhibited by the fusion protein comprising growth differentiation factor 11 and epidermal growth factor (i.e., GDF11-EGF) is similar to the activity of the group treated only with single protein, i.e., epidermal growth factor. In this regard, instead of being a full-length protein, each of growth differentiation factor 11 domain and epidermal growth factor domain in the fusion protein corresponds to the separate active domain that has been used for producing the fusion protein of the present invention, and, when the treatment is carried out with single protein or the fusion protein at same concentration, mole number of the fusion protein would be about ½ of the mole number of single protein. As such, if a similar free radical scavenging activity is shown at the same concentration, the fusion protein is recognized to have a free radical scavenging activity that is about 2 times higher than the free radical scavenging activity of single protein. Based on this result, it was found that the fusion protein of the present invention which comprises growth differentiation factor 11 and epidermal growth factor has an excellent anti-oxidation activity, and thus the fusion protein is expected to have an effect of preventing skin aging.

A sequence listing electronically submitted with the present application on Sep. 28, 2021 as an ASCII text file named 20210928_Q61321GR12_TU_SEQ, created on Sep. 16, 2021 and having a size of 6,000 bytes, is incorporated herein by reference in its entirety.

What is claimed is:

1. A fusion protein having the amino acid sequence of SEQ ID NO: 2 or SEQ ID NO: 4.

2. A gene encoding the fusion protein of claim 1.

3. The gene according to claim 2, wherein the gene consists of the nucleotide sequence of SEQ ID NO: 1 or SEQ ID NO: 3.

4. A recombinant vector comprising the gene of claim 2.

5. A host cell transformed with the recombinant vector of claim 4, wherein the host cell is *Escherichia coli* (*E. coli*).

6. A method for producing the fusion protein in a host cell, the method comprising:
   transforming the host cell with the recombinant vector of claim 4.

7. The method of claim 6, wherein the host cell is *E. coli*.

8. A composition comprising:
   a fusion protein having the amino acid sequence of SEQ ID NO: 2 or SEQ ID NO: 4.

9. The fusion protein of claim 1, wherein the amino acid sequence is SEQ ID NO: 2.

10. The fusion protein of claim 1, wherein the amino acid sequence is SEQ ID NO: 4.

11. The gene according to claim 2, wherein the gene has the nucleotide sequence of SEQ ID NO: 1.

12. The gene according to claim 2, wherein the gene has the nucleotide sequence of SEQ ID NO: 3.

13. A recombinant vector comprising the gene of claim 11.

14. A recombinant vector comprising the gene of claim 12.

15. A host cell transformed with the recombinant vector of claim 13, wherein the host cell is *Escherichia coli* (*E. coli*).

16. A host cell transformed with the recombinant vector of claim 14, wherein the host cell is *Escherichia coli* (*E. coli*).

17. A method for producing the fusion protein in a host cell, the method comprising:
   transforming the host cell with the recombinant vector of claim 13.

18. A method for producing in a host cell the fusion protein, the method comprising: transforming the host cell with the recombinant vector of claim 14.

19. A method for regenerating skin and improving skin wrinkle of a subject, the method comprising applying the composition of claim 8 to a skin of the subject.

* * * * *